US012678234B2

(12) United States Patent
Flexman et al.

(10) Patent No.: US 12,678,234 B2
(45) Date of Patent: Jul. 14, 2026

(54) SYSTEM FOR GUIDING INTERVENTIONAL INSTRUMENT TO INTERNAL TARGET

(71) Applicant: KONINKLIJKE PHILIPS N.V., Eindhoven (NL)

(72) Inventors: Molly Lara Flexman, Melrose, MA (US); Torre Michele Bydlon, Melrose, MA (US); Sean Kyne, Brookline, MA (US); Alvin Chen, Cambridge, MA (US)

(73) Assignee: KOINKLIJKE PHILIPS N.V., Eindhoven (NL)

( * ) Notice: Subject to any disclaimer, the term of this patent is extended or adjusted under 35 U.S.C. 154(b) by 528 days.

(21) Appl. No.: 18/008,019

(22) PCT Filed: Jun. 3, 2021

(86) PCT No.: PCT/EP2021/064918
§ 371 (c)(1),
(2) Date: Dec. 2, 2022

(87) PCT Pub. No.: WO2021/245193
PCT Pub. Date: Dec. 9, 2021

(65) Prior Publication Data
US 2023/0240757 A1 Aug. 3, 2023

Related U.S. Application Data

(60) Provisional application No. 63/035,019, filed on Jun. 5, 2020.

(51) Int. Cl.
*A61B 34/20* (2016.01)
*A61B 6/12* (2006.01)
*A61B 90/00* (2016.01)

(52) U.S. Cl.
CPC ............... *A61B 34/20* (2016.02); *A61B 6/12* (2013.01); *A61B 2090/376* (2016.02)

(58) Field of Classification Search
CPC ............ A61B 17/3403; A61B 17/3405; A61B 17/3407; A61B 2034/2061; A61B 34/20;
(Continued)

(56) References Cited

U.S. PATENT DOCUMENTS

| 10,675,099 B2 * | 6/2020 | Nakamura | ............. A61B 34/20 |
| 2010/0247513 A1 * | 9/2010 | Agee | ...................... A61B 17/32 |
| | | | 604/165.01 |

(Continued)

FOREIGN PATENT DOCUMENTS

| WO | 2016038489 A2 | 3/2016 |
| WO | 2018200799 A1 | 11/2018 |
| WO | 2019008127 A1 | 1/2019 |

OTHER PUBLICATIONS

Design of an actively controlled steerable needle with tendon actuation and FBG-based shape sensing, Nick J van de Berg et al., Medical Engg. & Phy., 37, 2015, pp. 617-622.
(Continued)

*Primary Examiner* — Adil Partap S Virk

(57) ABSTRACT

A system is provided for guiding an interventional instrument (150) to an internal target in a subject. The system includes a guide device (100) configured to rest on an outer surface of the subject and a shape sensing device (140). The guide device includes a holder (120) configured to receive the interventional instrument (150) and to provide an entry trajectory of the interventional instrument (150) for guiding the interventional instrument (150) to the target; and a fastener (130) attached to a portion of the guide device (100). The shape sensing device (140) provides shape sensing data indicating a shape of at least a portion of the shape sensing device (140) secured to the guide device (100) by
(Continued)

the fastener (130). The shape sensing data enables determination of a position and orientation of the guide device (100) on the outer surface of the subject.

24 Claims, 8 Drawing Sheets

(58) Field of Classification Search
CPC ................ A61B 6/12; A61B 2090/376; A61B 2034/107; A61B 2034/2051; A61B 2090/0807; A61B 2090/374; A61B 2090/3762; A61B 2090/378; A61B 2017/3407
See application file for complete search history.

(56)                    References Cited

U.S. PATENT DOCUMENTS

| | | | |
|---|---|---|---|
| 2013/0204124 A1 * | 8/2013 | Duindam | A61B 17/3468 604/272 |
| 2014/0114180 A1 | 4/2014 | Jain | |
| 2014/0343568 A1 | 11/2014 | Fenech et al. | |
| 2015/0254526 A1 | 9/2015 | Denissen | |
| 2016/0249991 A1 | 9/2016 | Glozman et al. | |
| 2017/0196591 A1 * | 7/2017 | Long, Jr. | A61B 17/3403 |
| 2017/0290563 A1 * | 10/2017 | Cole | A61M 25/0147 |
| 2018/0092701 A1 | 4/2018 | Fenech | |
| 2018/0279909 A1 | 10/2018 | Noonan et al. | |
| 2019/0167357 A1 | 6/2019 | Noonan et al. | |
| 2019/0282262 A1 * | 9/2019 | Bouazza-Marouf | A61B 17/3403 |
| 2020/0054378 A1 * | 2/2020 | Kincaid | A61B 6/12 |
| 2020/0121219 A1 * | 4/2020 | Ganesan | A61B 34/10 |

OTHER PUBLICATIONS

N. Gjin, B. Peter, M. Juliana, et al. Periprocedural bleeding and 1 year outcome after percutaneous coronary Intervention. JACC, 51 (2008), pp. 690-697.

Mehan V.K., Patil S., Patel M., An inexpensive, simple technique to improve the safety of femoral arterial puncture. Indian Heart Journal, 67 (2015), pp. 546-548.

Jung N, Kim D. Effect of electromagnetic navigated ventriculoperitoneal shunt placement on failure rates. J Korean Neurosurg Soc. 2013;53(3):150-154.

International Search report and Written Opinion of PCT/EP2021/064918, dated Nov. 16, 2021.

* cited by examiner

SYSTEM FOR GUIDING INTERVENTIONAL INSTRUMENT TO INTERNAL TARGET

CROSS-REFERENCE TO PRIOR APPLICATIONS

This application is the U.S. National Phase application under 35 U.S.C. § 371 of International Application No. PCT/EP2021/064918, filed on Jun. 3, 2021, which claims the benefit of U.S. Provisional Patent Application Ser. No. 63/035,019, filed Jun. 5, 2020. These applications are hereby incorporated by reference herein.

BACKGROUND

Minimally invasive procedures rely on the ability to accurately access an internal target, such as a vessel, an internal organ or a tumor, in the subject using an interventional instrument with little damage to the surrounding regions. Getting the correct location for percutaneous access to reach the internal target requires identifying an entry location (e.g., in x, y, z coordinates in a three-dimensional coordinate system) on the surface of the subject, as well as two angular adjustments to define an entry trajectory of the interventional instrument from the entry location to the internal target. Generally, providing navigational guidance may improve the targeting, and reduce procedure time. Also, to the extent x-ray imaging is used during the minimally invasive procedure, efficient navigational guidance reduces the x-ray dose to the subject otherwise required.

One option to provide guidance during percutaneous access is to integrate sensors directly into the interventional instrument itself. However, this has the disadvantage of requiring modification to the interventional instrument, which may be hindered by geometry constraints (e.g., for needles, in particular), the wide portfolio of available types of interventional instruments, and the various price points.

SUMMARY

According to an aspect of the present disclosure, a system is provided for guiding an interventional instrument to an internal target in a subject. The system includes a guide device configured to rest on an outer surface (e.g., skin) of the subject, the guide device including at least one holder configured to receive the interventional instrument and to guide the interventional instrument to the target according to an entry trajectory, and a fastener attached to or attachable to a portion of the guide device having a fixed shape with at least one identifiable shape feature. The system further includes a shape sensing device secured to the guide device by the fastener such that at least a portion of the shape sensing device secured to the guide device has the fixed shape with the at least one identifiable shape feature, the shape sensing device being arranged to provide shape sensing data relating to the fixed shape of the at least a portion of the shape sensing device secured to the guide device by the fastener.

The system may further include a processing unit and memory for storing instructions that, when executed by the processing unit, cause the processing unit to receive initial image data from an initial image of the target in the subject; define a location of the target in the initial image data; receive shape sensing data from the shape sensing device indicating the shape of the at least a portion of the shape sensing device attached to (e.g., inserted through a sleeve) the guide device; determine a position and orientation of the guide device using the shape sensing data; determine a position of the interventional instrument relative to the portion of the shape sending device attached to the guide device, including an entry point and an entry trajectory of the interventional instrument, using the shape sensing data; and display an indication of the determined position of the interventional instrument overlaid with the initial image of the region of interest on a display, enabling a user or a robot to maneuver the interventional instrument to the target using the initial image data and/or feedback from sensors on the guide device.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
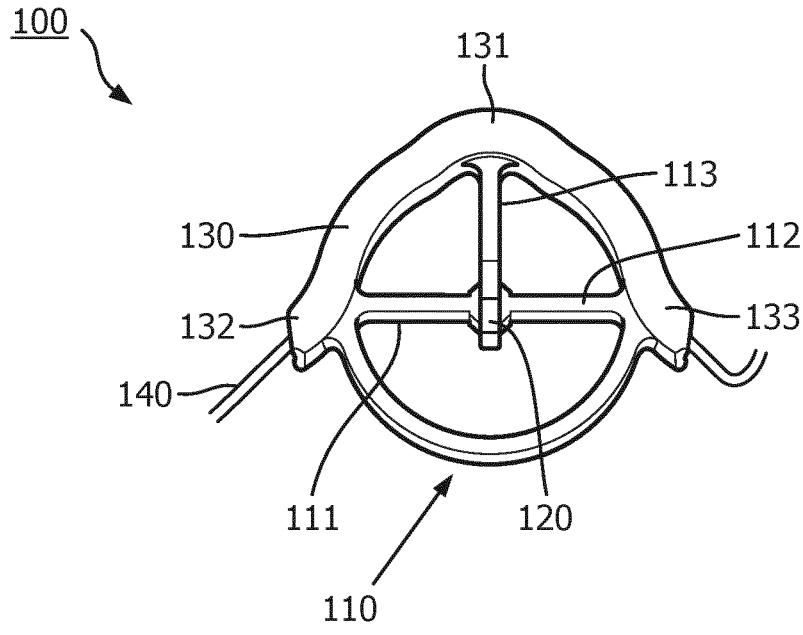
FIG. 1A is a plan view of a guide device with an optical shape sensing (OSS) device configured to guide an interventional instrument to an internal target in a subject, according to a representative embodiment.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a," "an" and "the" are intended to include both singular and plural forms, unless the context clearly dictates otherwise. Additionally, the terms "comprises," "comprising," and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

FIG. 1A is a plan view of a guide device with a shape sensing device configured to guide an interventional instrument to an internal target in a subject, according to a representative embodiment.

Referring to FIG. 1A, a guide device 100 is configured to rest on an outer surface (e.g., the skin) of the subject, and includes a support structure 110, a holder 120 configured to receive an interventional instrument (e.g., interventional instrument 150 shown in FIG. 1B) and to guide the interventional instrument toward the target according to an entry trajectory, and a fastener 130 attached to a portion of the support structure 110. The guide device 100 must be correctly located on the subject for percutaneous access, such that the interventional instrument intersects the target when it is advanced through the holder 120. This requires identifying the location in a three-dimensional (3D) coordinate system (x,y,z location) on the surface of the subject, as well as two angular adjustments to define an entry trajectory. Such navigation guidance improves access to the target by the interventional instrument, thereby reducing procedure time and eliminating or reducing the need for real time imaging. When imaging is provided by an x-ray system, this reduces the x-ray dose required during navigation.

In the depicted embodiment, the support structure 110 has an outer frame 115 that forms an outer perimeter of the guide device 100, and cross-supports that attach the holder 120 to the outer frame 115 across an open area within the outer perimeter of the guide device 100. The cross-supports include a first cross-support 111 and a second cross-support 112 arranged in a first direction across the open area, and a third cross-support 113 arranged in a second direction that is substantially perpendicular to the first direction. The first, second and third cross-supports 111, 112 and 113 thereby secure the holder 120 to the outer frame 115.

The guide device 100 may be rigid or flexible. That is, in an embodiment, the support structure 110 may be formed of a flexible material, such as silicone rubber, for example. This enables the support structure 110 to be deformable against the outer layer of the subject, which may assist in guiding the interventional instrument toward the target by adding degrees of freedom to the entry trajectory options provided by the holder 120. Alternatively, the support structure 110 may be formed of a substantially rigid material, such as acrylonitrile butadiene styrene (ABS) or other thermoplastic polymer, for example, which may increase durability.

In the depicted embodiment, the outer frame 115 of the support structure 110 is substantially circular in shape, and the holder 120 is secured by three representative cross-supports, i.e., the first, second and third cross-supports 111, 112 and 113, for purposes of illustration. It is understood, however, that the outer frame 115 may have any of a variety of different shapes, such as square, rectangular, triangular, ellipsoidal and trapezoidal, for example, without departing from the scope of the present. It is further understood that the support structure 110 may have more or fewer than three cross-supports for securing the holder 120 arranged at any angles relative to one another, without departing from the scope of the present. Alternatively, the holder 120 may be secured by material that substantially fills the open area defined by the outer frame 115, without departing from the scope of the present.

The fastener 130 is configured to receive a shape sensing device 140, such as an elongated optical shape sensing (OSS) device, securing it to a portion of the support structure 110 in a manner that causes the shape sensing device 140 to maintain a recognizable, fixed shape relative to the support structure 110, where the fixed shape has at least one identifiable shape feature. For example, the fastener 130 may adopt the shape of the portion of the support structure 110 to which it is attached, such that the at least one identifiable shape feature is a shape, e.g., a curved portion, of the shape sensing device 140. Of course, other identifiable shape features, such as one or more protrusions and/or one or more recesses, may be incorporated without departing from the scope of the present teachings. In the depicted embodiment, the fastener 130 is implemented as a sleeve through which the shape sensing device 140 is inserted. The sleeve may be formed of polytetrefluoroethylene (PTFE) plastic tubing, for example, although any compatible material may be incorporated. Also in the depicted embodiment, the fastener 130 takes on the shape of the portion of the perimeter of the support structure 110 to which it is attached, which in this case is the shape of an upper portion of the outer frame 115. In alternative embodiments, the fastener 130 may be any device or structure capable of securing the shape sensing device 140 to the support structure 110 of the guide device 100, such that the shape sensing device has a recognizable fixed shape and/or other identifiable shape features. For example, the fastener 130 may include a "U" channel formed along a portion of the outer frame 115, where the shape sensing device 140 is press fit into the "U" channel. Alternatively, the fastener 130 may include one or more clips that are attached or attachable to the guide device 100, and that attach the shape sensing device 140 to a portion of the outer frame 115.

In the depicted embodiment, the outer frame 115 has a unique shape or curvature profile, including one or more distinctive shape characteristics, which are translated to the pathway defined by the fastener 130 as identifiable shape features by virtue of its attachment to the outer frame 115. The unique shape allows for detection of the guide device 100, and alignment of the guide device 100 to the shape sensing device 140. In the depicted embodiment, the outer frame 115 includes three representative shape characteristics that are nodules protruding from the otherwise circular outer perimeter of the support structure 110. That is, the outer frame 115, and thus the fastener 130, includes a first protrusion 131 at a 12 o'clock position (frame apex), a second protrusion 132 at a 9 o'clock position (OSS device entry location), and a third protrusion 133 at a 3 o'clock position (OSS device exit location) of the outer frame 115.

The shape sensing device 140 may be an OSS device, for example, that includes one or more optical fibers with integrated fiber Bragg gratings (FBGs) used as strain sensors for detecting shape information and providing shape sensing data indicating the shape of the shape sensing device 140, as is well known to one of ordinary skill in the art. The shape sensing device 140 may be implemented by any shape sensing device that is insertable into or otherwise secured by the fastener 130, such as a guide wire, a catheter, or a sheath, for example. For example, the shape sensing device 140 may be implemented using Fiber Optic RealShape (FORS) technology, in which case the shape sensing data comprises FORS data that includes but is not limited to the 3D shape of the shape sensing device 140, curvature, and axial strain. In alternative embodiments, the shape sensing device 140 may be implemented using shape sensing technology other than optical shape sensing. For example, the shape sensing device 140 may include transducers, electrodes and/or electromagnetic sensors arranged along at least a portion of the shape sensing device such that the device shape may be determined. For example, if three or more electromagnetic sensors are attached to the shape sensing device 140, then a shape and/or other identifiable shape features may be determined from the three positions thus providing a location and orientation for the guide device 100. Generally, the more sensors that are arranged on the shape sensing device 140 would provide better shape resolution and accuracy. Generally, the guide device 100 includes specific features in the insert path of the interventional instrument that can be detected in the shape profile (e.g., curvature, strain, temperature) provided by the shape sensing device 140.

Since the shape sensing device 140 is inserted in or otherwise attached to the fastener 130, the shape sensing data provided by the shape sensing device 140 indicates the shape of the fastener 130, and thus the shape and/or other identifiable shape features of the upper portion of the outer frame 115 to which the fastener 130 is attached. Accordingly, the location of the upper portion of the outer frame 115 may be located in a 3D coordinate system based on this distinctive shape sensing data. Also, the first, second and third protrusions 131, 132 and 133 enable the shape sensing device 140 to accurately indicate specific sections of the upper portion of the outer frame 115. Once the location of the upper portion of the outer frame 115 is determined, the location of the holder 120 can likewise be determined, which also is the location of an initial insertion point of the interventional instrument. Accordingly, the location of the initial insertion point of the interventional instrument can be determined in the 3D coordinate system using the shape sensing data provided by the shape sensing device 140. Assuming that the shape sensing data and the anatomy are in the same 3D coordinate system, then the initial insertion point location can be found without requiring additional medical imaging. Generally, the medical imaging 3D coordinate system (or anatomy 3D coordinate system) and the shape sensing 3D coordinate system must be aligned (or registered) in the same 3D coordinate system to know where the initial insertion point should be, as would be known to one skilled in the art.

As mentioned above, the holder 120 may provide at least one channel, for example, which is configured to receive the interventional instrument, providing an entry trajectory of the interventional instrument at the initial insertion point on the surface of the subject in order to guide the interventional instrument to the target. In various embodiments, the holder 120 may be implemented using other compatible means, such as a gripping mechanism which grips the interventional instrument, then periodically releases it according to insertion steps so as to drive the interventional instrument toward the target according to the entry trajectory, step-by-step, as described, for example, by U.S. Patent App. Pub. No. 2016/0249991 (published Sep. 1, 2016), entitled "Gripper for Robotic Image Guided Needle Insertion," which is hereby incorporated by reference in its entirety, in which such holder is integrated in a robotic system. The entry trajectory is the angle of entry of the interventional instrument relative to a plane defined by a bottom surface of the support structure 110 of the guide device 100 (which may be substantially the same as a plane defined by the outer surface of the subject). This entry trajectory combined with the determined location of the insertion point, discussed above, enables determination of where the interventional instrument is located in the subject with respect to the target, particularly when the length of the interventional instrument is known.

Figure 1B:
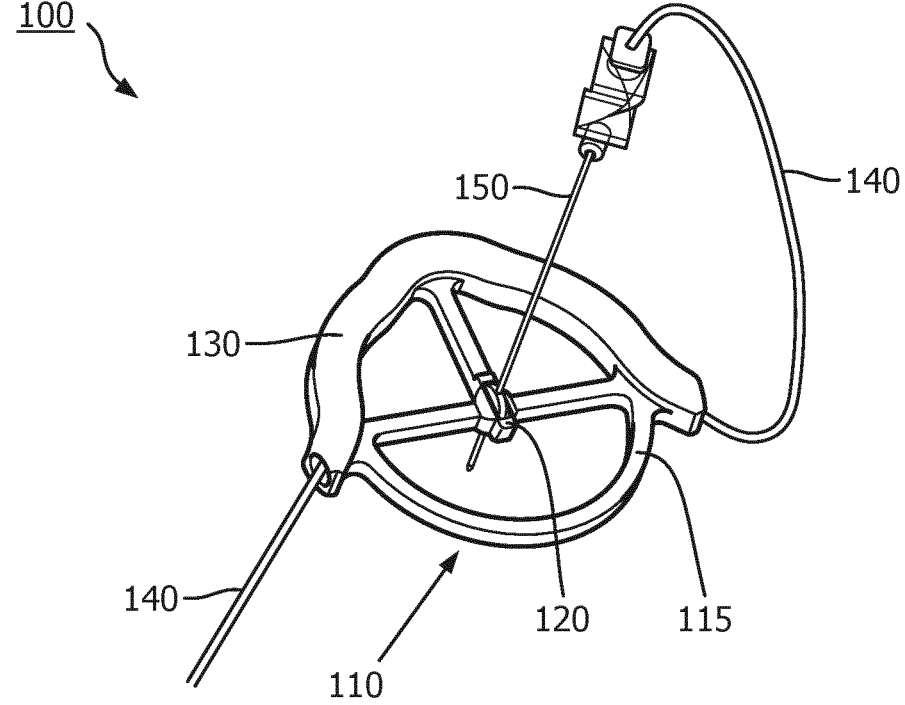
FIG. 1B is a plan view of a guide device with shape sensing device attached to the interventional instrument for guiding the interventional instrument to an internal target in a subject, according to a representative embodiment.

FIG. 1B is a plan view of a guide device with a shape sensing device attached to the interventional instrument for guiding the interventional instrument to an internal target in a subject, according to a representative embodiment.

Referring to FIG. 1B, an embodiment of the guide device 100 is depicted where a distal end of the shape sensing device 140 is connected to a proximal end of interventional instrument 150. The interventional instrument 150 is inserted in a channel or other trajectory guide formed by the holder 120 at a selected entry trajectory. Because the shape sensing device 140 is connected to the interventional instrument 150, the shape sensing data may be further used to determine the length, position and orientation of the interventional instrument 150 in the 3D coordinate system. For example, the dynamic component (e.g., the z-axis of the interventional instrument 150) can be tracked when the shape sensing device 140 is connected to the interventional instrument 150.

Figure 2A:
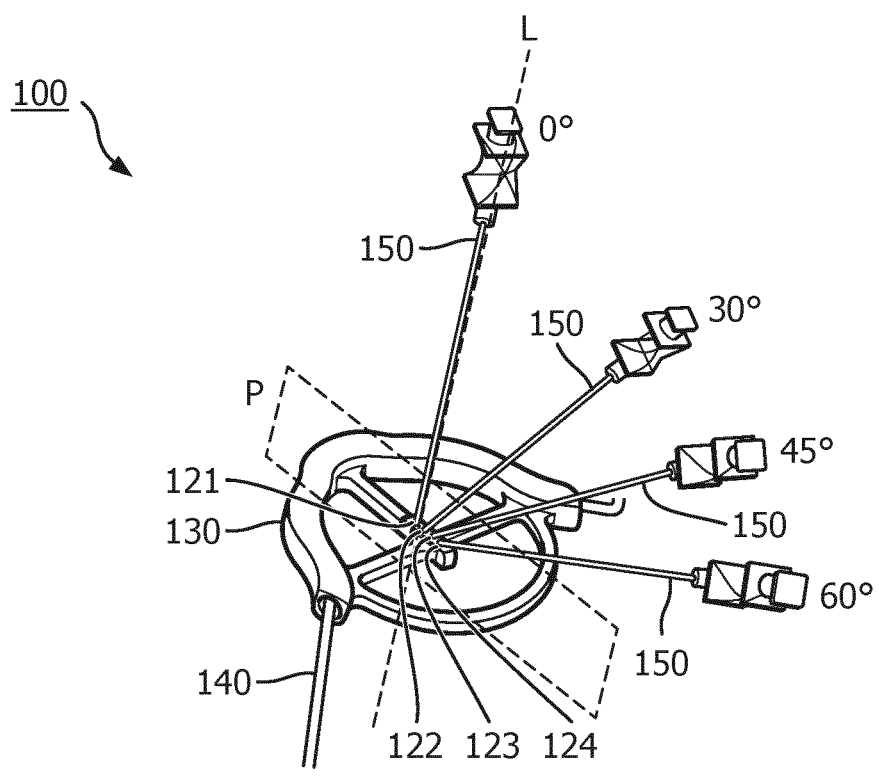
FIG. 2A is a plan view of a holder including discrete guide channels corresponding to different entry trajectories for guiding the interventional instrument, according to a representative embodiment.
Figure 2B:
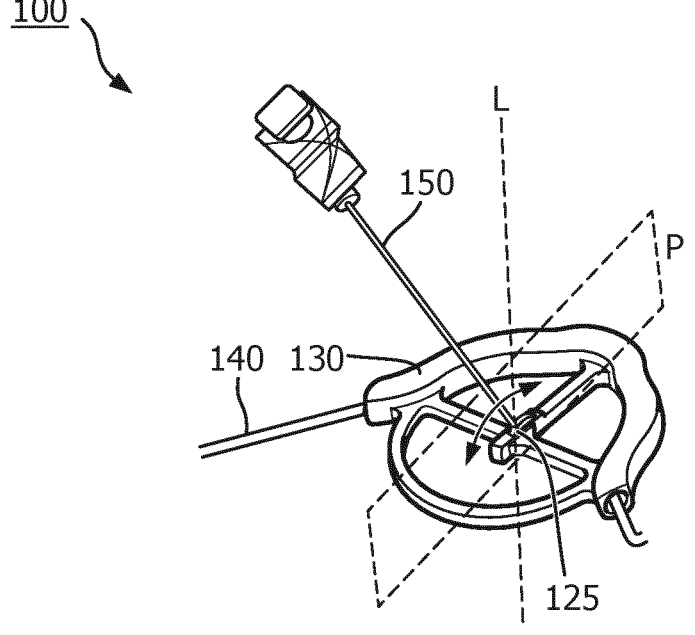
FIG. 2B is a plan view of a holder including a single, pivoting guide channel providing a range of entry trajectories for guiding the interventional instrument, according to a representative embodiment.

FIGS. 2A and 2B depict embodiments of the holder 120 for guiding the interventional instrument into the subject at a desired entry trajectory. In particular, FIG. 2A is a plan view of a holder including multiple fixed guide channels corresponding to different entry trajectories for guiding the interventional instrument, according to a representative embodiment, and FIG. 2B is a plan view of a holder including a single, pivoting guide channel providing a range of entry trajectories for guiding the interventional instrument, according to a representative embodiment.

Referring to FIG. 2A, the holder 120 includes four fixed guide channels corresponding to four entry trajectories, respectively, relative to a reference line L (indicated as a dashed line) in a reference plane P that is substantially perpendicular to a plane defined by the bottom surface of the support structure 110. In the depicted example, the holder 120 includes a first fixed channel 121 at a zero degree angle relative to the reference line L, a second fixed channel 122 at a 30 degree angle relative to the reference line L, a third fixed channel 123 at a 45 degree angle relative to the reference line L, and a fourth fixed channel 124 at a 60 degree angle relative to the reference line L. Of course, the holder 120 may include more or fewer fixed guide channels at the same or different angles, without departing from the scope of the present teachings.

FIG. 2A also shows a representative interventional instrument 150 (e.g., a needle, cannula, sheath, introducer) at four different orientations corresponding to the four different entry trajectories defined by insertion in the first, second, third and fourth fixed channels 121, 122, 123 and 124, respectively. Or course, in operation, the interventional instrument 150 would be inserted by a user in only one of the first, second, third and fourth fixed channels 121, 122, 123 and 124 at a time, depending on the entry trajectory needed to reach the target in the subject. Also, for purposes of illustration, the first, second, third and fourth fixed channels 121, 122, 123 and 124 are all in a plane P that is substantially perpendicular to the reference plane defined by the support structure 110. In an embodiment, the interventional instrument 150 may be inserted in the desired channel a robot configured to control the positioning and insertion of the interventional instrument.

Referring to FIG. 2B, the holder 120 includes a single pivoting channel 125 configured to rotate through a continuous range of entry trajectories (indicated by an arrow) within a plane P, which may be substantially perpendicular to the reference plane defined by the support structure 110 for purposes of illustration. The pivoting channel 125 may be rotatably connected to the support structure 110 by a pivot joint, for example, that allows the pivoting channel 125 to pivot through the continuous range of entry trajectories. The entry trajectory of the interventional instrument 150 is set by a user selecting a selected angle of the pivoting channel 125 within the continuous range of entry trajectories. In the depicted example, the continuous range of entry trajectories goes from about a 60 degree angle (e.g., negative) on one side of a reference line L (indicated as a dashed line), which is substantially perpendicular to the reference plane defined by the support structure 110, to about a 60 degree angle (positive) on the opposite side of the reference line L, for an approximately 120 degree continuous range. In an embodiment, the entry trajectory of the interventional instrument 150 may be set by a robot using the pivoting channel 125, where the robot is configured to control the positioning and insertion of the interventional instrument.

The value of the selected angle may be identified by the user using a scale or other angular encoding indicator on the pivoting channel 125. Also, in an embodiment in which the distal end of the shape sensing device 140 is connected to the proximal end of the interventional instrument 150, mentioned above, the value of the selected angle may be identified using the shape sensing data provided by the shape sensing device 140. For example, the location of the pivoting channel 125 may be determined relative to the upper portion of the outer frame 115, indicating a first point corresponding to the distal end of the interventional instrument 150, and the location of the distal end of the shape sensing device 140 may likewise be determined relative to the upper portion of the outer frame 115 and/or to the first point, indicating a second point corresponding to the proximal end of the interventional instrument 150. The relative angle between the first and second points may then be calculated, providing the selected angle of the pivoting channel 125.

Figure 3:
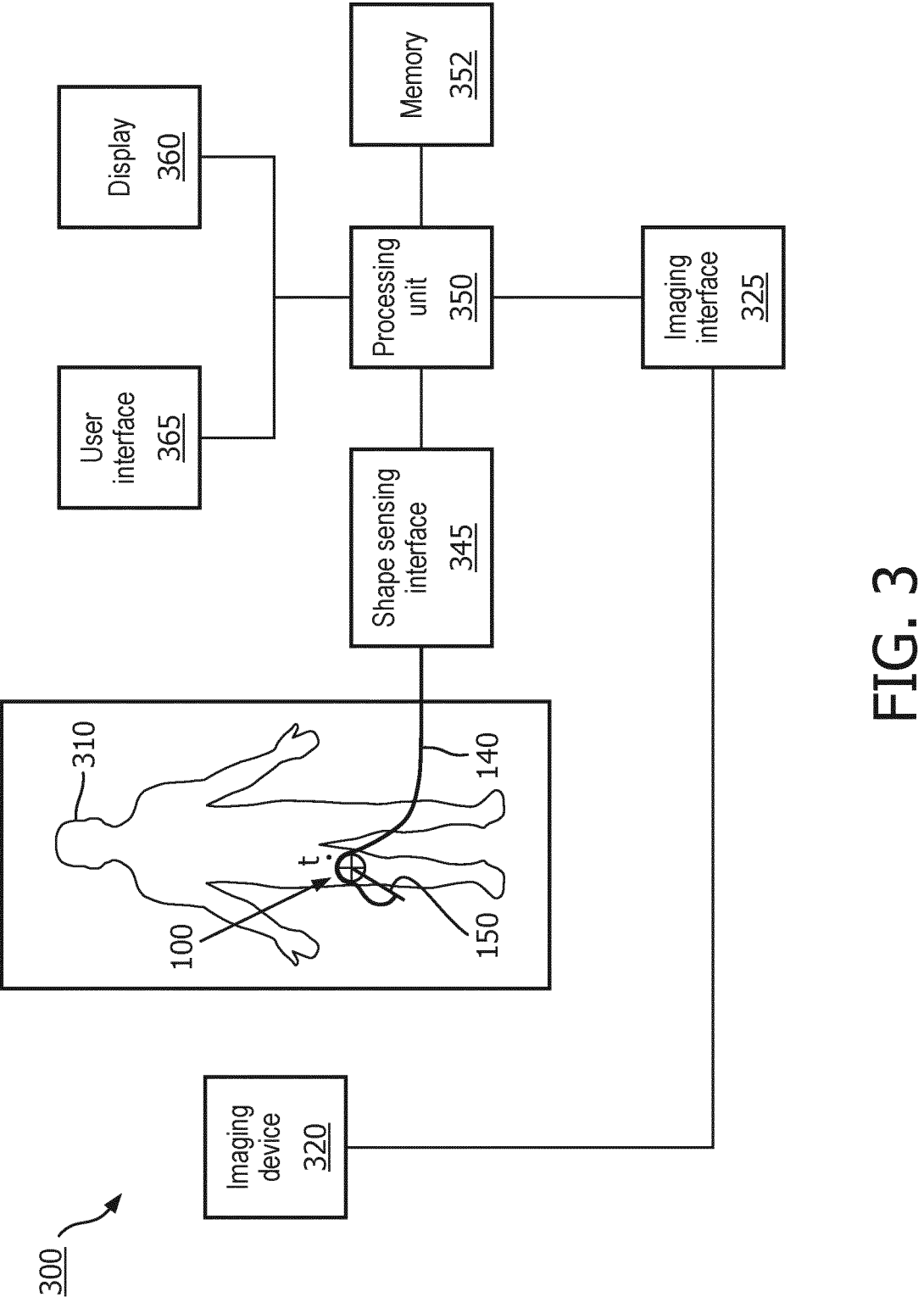
FIG. 3 is a simplified block diagram of a guidance system including a guide device for guiding an interventional instrument to the internal target within the subject, according to a representative embodiment.

FIG. 3 is a simplified block diagram of a guidance system, including the guide device 100, for guiding the interventional instrument 150 to a target within the subject, according to a representative embodiment.

Referring to FIG. 3, a guidance system 300 includes guide device 100, shape sensing device 140, a processing unit 350 and memory 352 for guiding interventional instrument 150 to an internal target t of a subject 320. In an embodiment, the processing unit 350 and the memory 352 may be implemented in a controller, for example. Also, in an embodiment, the interventional instrument 150 may be guided to the internal target t by a robot (not shown) in response to entry trajectory and positioning information provided by the shape sensing data. The target t may be a predetermined location in an artery or vessel in the leg of the subject 310, for example, and the interventional instrument 150 may be a needle for accessing the artery at the predetermined point. Alternatively, the target t may be a tumor, a blood clot or other abnormality, for example, and the interventional instrument 150 may be a device for imaging, treating and/or removing the abnormality. The shape sensing device 140 may be an OSS shape sensing device, for example, which communicates with the processing unit 350 through a shape sensing interface 345 over a wired or wireless network connection. That is, the shape sensing device 140 receives control commands and provides shape sensing data from and to the processing unit 350 through the shape sensing interface 345.

The guidance system 300 communicates with an imaging device 320 configured to acquire images of a region of interest that includes the target tin the subject 320, and to provide corresponding image data to the processing unit 350. The imaging device 320 acquires at least one image of the target t before the interventional instrument 150 is guided to the target t using the guide device 100. The image data is used to determine the initial location of the target t. The imaging device 320 may be any type of medical imaging device capable of providing images of an internal target, including an x-ray imaging device that provides x-ray, CT and/or fluoroscopy image data, an ultrasound imaging device that provides ultrasound image data, or a magnetic resonance imaging (MRI) imaging device that provides MRI image, for example. The imaging device 320 communicates with the processing unit 350 through an imaging interface 325 over a wired or wireless network connection. That is, the imaging device 320 receives control commands from the processing unit 350 and provides imaging data to the processing unit 350 in response through the imaging interface 325.

The shape sensing data provided by the shape sensing device 140 are registered to the image data provided by the imaging device 320, so that the shape sensing data are provided in the same 3D coordinate system as the image data, as well as the location of the target t in the image data. This registration may be achieved in various ways, as would be known to one skilled in the art. For example, the registration may use one or two x-ray images provided by the imaging device 320 with the shape sensing device 140 visible in the field of view of the x-ray images. The 3D coordinate systems of the imaging device 320 and the shape sensing device 140 may then be aligned, using a manual process of identifying a portion of the shape sensing device 140 in the images or an automatic image processing algorithm to locate the shape sensing device 140, and knowing geometry information about the imaging device 320 (x-ray system). Examples related to registering shape sensing data and imaging data are provided by U.S. Patent App. Pub. No. 2014/0114180 (published Apr. 24, 2014), entitled "Live 3D Angiogram using Registration of a Surgical Tool Curve to an X-ray Image," and U.S. Patent App. Pub. No. 2015/0254526 (published Sep. 10, 2015), entitled "Three Dimensional Polyline Registration using Shape Constraints," which are hereby incorporated by reference in their entireties.

Figure 4:
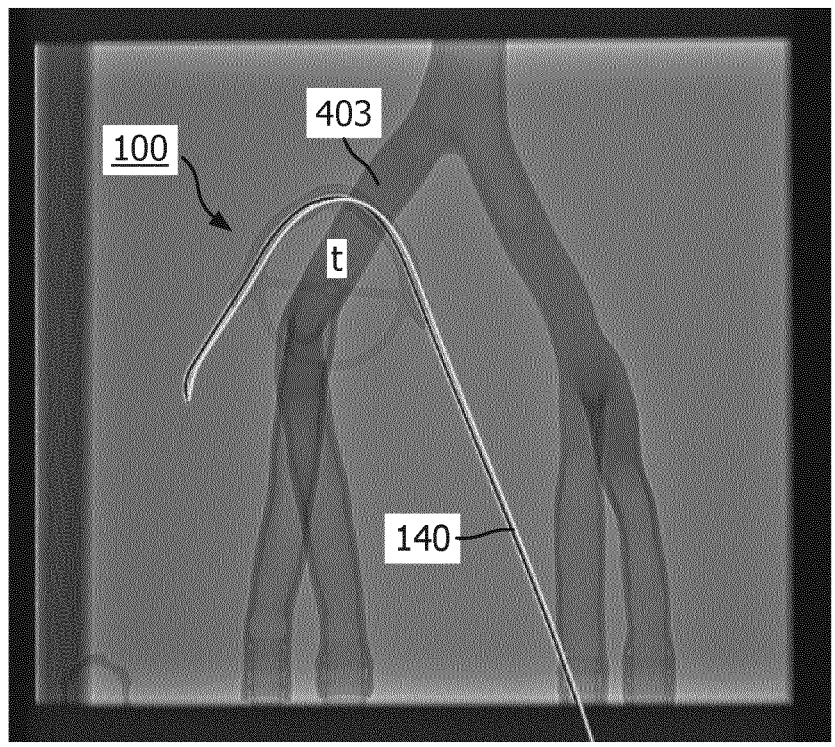
FIG. 4 is an initial x-ray image of the internal target with the guide device in the field of view, according to a representative embodiment.

The image may also include an image of all or part of the guide device 100, which may be helpful in determining relative initial locations of the guide device 100 and the target t. For example, assuming that the imaging device 320 is an x-ray imaging device, FIG. 4 shows an initial x-ray image by the imaging device 320 of the target tin an artery 430 with the guide device 100 in the field of view, according to a representative embodiment. The x-ray image further shows a portion of the shape sensing device 140, enabling simultaneous visualization of the target t, the guide device 100 and the shape sensing device 140. The processing unit 350 is able to determine the relative initial locations of the guide device 100 and the target t using the image data from the x-ray image.

When the imaging device 320 provides real time images throughout the guidance process, as in the case of fluoroscopy or ultrasound imaging, the processing unit 350 may implement a dynamic, continuous re-registration process in order to compensate for deformable tissue in the subject 310. For example, when the target t is in a vessel that is rolling and/or being pushed aside due to pressure induced by the guide device 100 on the skin surface of the subject 310 or by the advancement of the interventional instrument 150, the target t will be in a moving location. In this case, the processing unit 350 continuously updates the target location, and likewise determines corresponding adjustments with regard to the position and orientation of the guide device 100 and/or the interventional instrument 150.

In the depicted embodiment, the processing unit 350, together with the memory 352, implements at least a portion of a method for guiding the interventional instrument 150 to the target tin the subject 310, and may be configured to perform and/or control all or a portion of the steps of the process shown in FIG. 9, discussed below. In various embodiments, the processing unit 350 may include one or more computer processors, digital signal processors (DSPs), central processing units (CPUs), graphics processing units (GPUs), remote application program interfaces (APIs), field-programmable gate arrays (FPGAs), application specific integrated circuits (ASICs), or combinations thereof, using any combination of hardware, software, firmware, hard-wired logic circuits, or combinations thereof. The processing unit 350 may include its own processing memory for storing computer readable code (e.g., software, software modules, software engines) that enables performance of the various functions described herein.

The term "processor" as used herein encompasses an electronic component able to execute a program or machine executable instruction, and should be interpreted to include more than one processor or processing core, as in a multi-core processor. A processor may also refer to a collection of processors within a single computer system or distributed among multiple computer systems. Programs have software instructions performed by one or multiple processors that may be within the same computing device or which may be distributed across multiple computing devices.

The memory 352 is representative of one or more memories and databases, including the processing memory, as well as multiple memories and databases, including distributed and networked memories and databases. The memory 352 may be various types of random access memory (RAM), read only memory (ROM) and/or other storage media, including flash memory, electrically programmable read-only memory (EPROM), electrically erasable and programmable read only memory (EEPROM), compact disk read only memory (CD-ROM), digital versatile disk (DVD), registers, latches, flip-flops, a hard disk, a removable disk, tape, floppy disk, blu-ray disk, or universal serial bus (USB) driver, or any other form of storage medium known in the art, which are tangible and non-transitory (e.g., as compared to transitory propagating signals). As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The memory 352 may store software instructions and/or computer readable code that enables performance of various functions. The memory 352 may be volatile or non-volatile, secure and/or encrypted, or unsecure and/or unencrypted, without departing from the scope of the present teachings.

"Memory" and "database" are examples of computer-readable storage media, and should be interpreted as possibly being multiple memories or databases. As stated above, the memory or database may for instance be multiple memories or databases local to the computer, and/or distributed amongst multiple computer systems or computing devices.

The user interface 365 is configured to provide information and data output by the processing unit 350 and/or the memory 352 to the user and/or for receiving information and data input by the user, and may include a network interface. That is, the user interface 365 enables the user to enter data and to control or manipulate aspects of guiding the interventional instrument 150 to the target t, and also enables the processing unit 350 to indicate the effects of the user's control or manipulation. The user interface 365 may include one or more of ports, disk drives, wireless antennas, or other types of receiver circuitry. The user interface 365 may further connect one or more user interfaces, such as a mouse, a keyboard, a mouse, a trackball, a joystick, a microphone, a video camera, a touchpad, a touchscreen, voice or gesture recognition captured by a microphone or video camera, for example.

The display 360 may be a monitor such as a computer monitor, a television, a liquid crystal display (LCD), an organic light emitting diode (OLED), a flat panel display, a solid-state display, or a cathode ray tube (CRT) display, or an electronic whiteboard, for example. The display 360 may include one or more display interface(s), in combination with the user interface 365, in which case the display 360 may provide a graphical user interface (GUI) for displaying and receiving information to and from the user.

In FIG. 3, the distal end of shape sensing device 140 is connected to the proximal end of the interventional instrument 150, as discussed above with reference to FIG. 1B. In this configuration, additional information may be determined by the processing unit 350 from the shape sensing data provided by the shape sensing device 140. For example, with the shape sensing device 140 connected to the interventional instrument 150, the shape sensing data indicates the position of both the distal and proximal ends of the interventional instrument 150 in the 3D coordinate system, where the distal end of the interventional instrument 150 initially coincides with the location of the holder 120 in the 3D coordinate system. Accordingly, the processing unit 350 is able to calculate the length of the interventional instrument 150 by determining the difference between the distal and proximal ends.

Once determined (or otherwise known), the length of the interventional instrument 150 may be used to track the distal end of the interventional instrument 150 (e.g., the tip of the needle) as it is advanced into the subject 310 through the guide device 100. That is, the distance between the proximal end of the interventional instrument 150 and the holder 120 becomes shorter as the interventional instrument 150 advances toward the target t through the at least one channel of the guide device 100. The processing unit 350 is able to continually determine this distance using the shape sensing data. Thus, the processing unit 350 is able to calculate the location of the distal end of the interventional instrument 150 by simply determining the remaining length of the interventional instrument 150, which is inside the subject, and determining the distal end to be the remaining length from the holder 120 at the entry trajectory. Also, as mentioned above, the processing unit 350 is able to calculate the entry trajectory of the interventional instrument 150 by determining the angle between the distance and proximal ends.

Figure 5A:
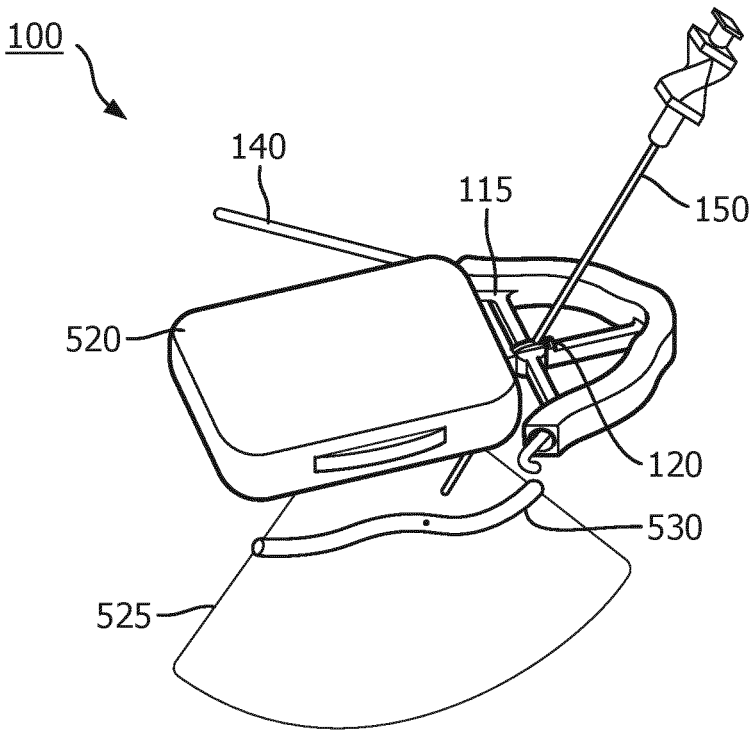
FIG. 5A is a top plan view of a guide device integrated with an ultrasound probe for guiding an interventional instrument to an internal target in a subject, according to a representative embodiment.
Figure 5B:
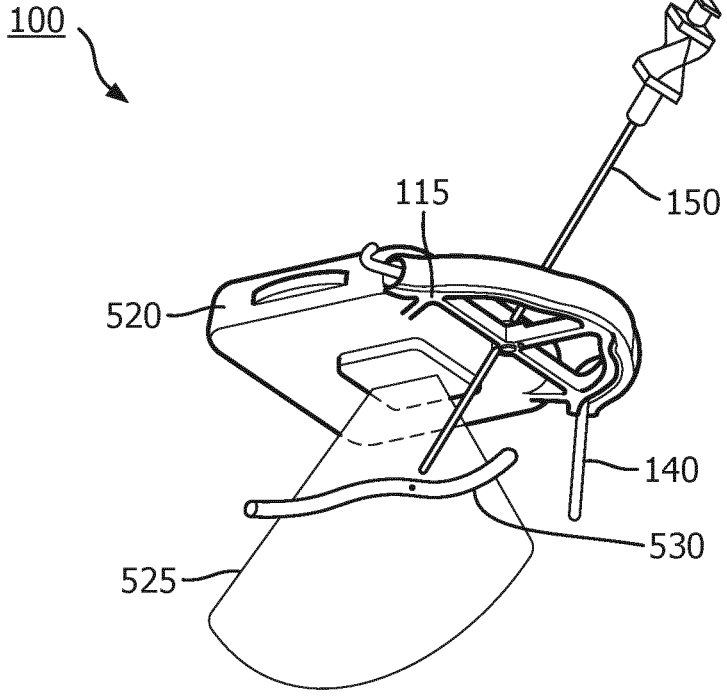
FIG. 5B is a bottom plan view of a guide device integrated with an ultrasound probe for guiding an interventional instrument to an internal target in a subject, according to a representative embodiment.

In various embodiments, a guide device may be integrated with another imaging device, e.g., in addition to the imaging device 320, in order to receive feedback in real time of movement of the interventional instrument through the guide device. FIGS. 5A and 5B are top and bottom plan views of a guide device integrated with an ultrasound probe for guiding an interventional instrument to an internal target in a subject, according to a representative embodiment.

Referring to FIGS. 5A and 5B, the guide device 100 is shown integrated with an ultrasound probe 520, which may be a portable wireless "puck" ultrasound probe, for example, although other types of ultrasound probes may be incorporated without departing from the scope of the present teachings. In the depicted embodiment, the guide device 100 is physically integrated with the ultrasound probe 520, as well as computationally integrated in that the guide device 100 and the ultrasound probe 520 are registered to the same three-coordinate system, as discussed above. In an alternative embodiment, the guide device 100 and the ultrasound probe 520 are integrated in that they are registered to the same three-coordinate system, but they are not physically integrated (i.e., they are unattached or physically separated).

More particularly, the ultrasound probe 520 is connected to the lower portion of the outer frame 115, and arranged such that a bottom surface of the ultrasound probe 520 is on substantially the same plane as a bottom surface of the outer frame 115. In this way, the ultrasound probe 520 and the outer frame 115 are immediately adjacent to one another, in a fixed mechanical relationship, on the outer surface of the subject 310. The ultrasound probe 520 emits sound waves in a field of view 525 into the subject 310 to obtain ultrasound images of the interventional instrument 150 and the target t, which in the depicted example is a location in an artery 530. The corresponding ultrasound image data may be sent to the processing unit 350 for processing via an ultrasound interface (not shown). The progress of the interventional instrument 150 may therefore be tracked in real time using both the shape sensing data provided by the shape sensing device 140 and the ultrasound probe 520. The target t and/or the vessel, artery or other structure containing the target t may also be tracked continuously with the ultrasound probe 520 to monitor any deformation or movement of the same. When the target t moves, this information can be determined by the processing unit 350, which updates the desired target location on the user interface 365 and/or the display 360.

Figure 6:
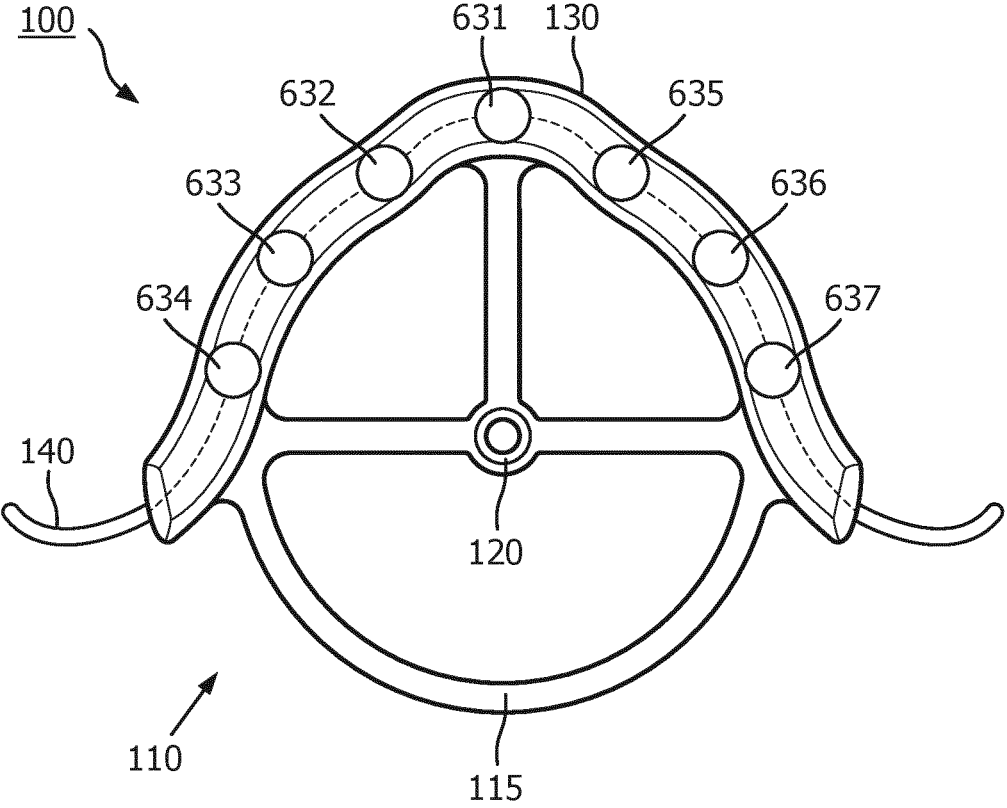
FIG. 6 is a plan view of a guide device with visual indicators for guiding an interventional instrument to an internal target in a subject, according to a representative embodiment.

A guide device may also include visual, audible and/or haptic indicators to direct the user how to move or reorient the guide device, such that the interventional instrument can be accurately advanced to the target. FIG. 6 is a plan view of a guide device with indicators for guiding an interventional instrument to an internal target in a subject, according to a representative embodiment.

Referring to FIG. 6, guide device 100 further includes representative indicators arranged on the fastener 130 configured to indicate a desired direction of rotation and/or a desired repositioning of the guide device 100 on the outer surface of the subject in order to guide the interventional instrument to the target. Alternatively, the indicators may be arranged on the support structure 110 of the guide device 100. In the depicted example, the representative indicators are visual indicators, such as light emitting diodes (LEDs), for example, that are configured to emit light to indicate the desired direction of rotation of the guide device 100 and/or a direction of movement of the guide device 100 toward the desired position on the surface of the subject. That is, a first visual indicator 631 is positioned at center, top of the of the support structure 110. A second visual indicator 632, a third visual indicator 633 and a fourth visual indicator 634 are arranged in order from the first visual indicator 631 along the left side of the fastener 130, and a fifth visual indicator 635, a sixth visual indicator 636 and a seventh visual indicator 637 are arranged in order from the first visual indicator 631 along the right side of the fastener 130. The first through seventh visual indicators 631-637 are selectively illuminated to indicate to the user whether and how to move the guide device 100 in order to properly guide the interventional instrument to the target.

The first through seventh visual indicators 631-637 may be configured to selectively illuminate in a rotation mode or in a repositioning mode, which may be selected by the user, e.g., via processing unit 350. In the rotation mode, the first visual indicator 631 illuminates when the guide device 100 is pointed in the correct direction. (Alternatively, no visual indicators may illuminate when the guide device 100 is pointed in the correct direction.) This means that, when advanced through the holder 120, the interventional instrument 150 will intersect the target with the guide device in its current rotational orientation. The remaining visual indicators illuminate to indicate the direction and amount of rotation when the guide device 100 is not pointed in the correct direction. So, the second, third and fourth visual indicators 632-634 illuminate to indicate counterclockwise rotation in an amount indicated by their respective positions. That is, illumination of the second visual indicator 632 indicates a lesser amount of counterclockwise rotation than illumination of the third or fourth visual indicators 633 or 634. Likewise, the fifth, sixth and seventh visual indicators 635-637 illuminate to indicate clockwise rotation in an amount indicated by their respective positions. That is, illumination of the fifth visual indicator 635 indicates a lesser amount of clockwise rotation than illumination of the sixth or seventh visual indicators 636 or 637. Alternatively, the first through seventh visual indicators 631-637 may illuminate in different colors to indicate the direction of rotation. For example, the selected visual indicator may illuminate green, while the unselected visual indicators may illuminate red.

In order to determine the amount of rotation, the processing unit 350 determines a projected location of the distal end of the interventional instrument 150 if it were to be guided through the holder 120 at the current entry trajectory with the guide device 100 in the current orientation. The location of the target is known from the initial image data, the orientation of the guide device 100 is known from the shape sensing data, and the length and orientation of the interventional instrument 150 is known or may be determined from the shape sensing data. The projected location will match the target location, or will be to the left or right by a determined amount. Accordingly, the processing unit 350 may control the first visual indicator 631 to illuminate when the projected location matches the target location, may control one of the second to fourth visual indicators 632-634 to illuminate when the projected location is to the right of the target location by an amount corresponding to the illuminated visual indicator, and may control one of the fifth to seventh visual sensors 635-637 to illuminate when the projected location is to the left of the target location by an amount corresponding to the illuminated visual indicator. The user then manually rotates the guide device 100 as indicated by the illuminated visual indicator.

In the position mode, the visual indicators are selectively illuminated indicate a direction for the user to move the guide device 100 based on an offset of the guide device 100 from a desired location. Accordingly, the first visual indicator 631 illuminates to indicate planned movement of the guide device 100 directly ahead, one of the second, third or fourth visual indicators 632-634 illuminates to indicate planned movement of the guide device at corresponding movement angle to the left, and one of the fifth, sixth or seventh visual indicators 635-637 illuminates to indicate planned movement of the guide device at a corresponding movement angle to the right. In an embodiment, the brightness and/or color of the illuminated indicator may also be adjusted to indicate a corresponding distance of the planned movement, e.g., the brighter the illumination, the further the guide device is to be moved in the indicated direction to cover a larger offset. Alternatively, the first through seventh visual indicators 631-637 may illuminate in different colors to indicate the direction of repositioning. For example, the selected visual indicator indicating the desired direction of movement may illuminate green, while the unselected visual indicators may illuminate red.

In order to determine the amount of movement, the processing unit 350 determines a projected location of the distal end of the interventional instrument 150 if it were to be guided through the holder 120 at the current entry trajectory with the guide device 100 in the current position on the subject. Again, the location of the target is known from the initial image data, and the initial location of the guide device 100 on the surface of the subject 310 is known from the shape sensing device 140 and the initial registration between the shape sensing device 140 and the initial image data. Also, the orientation of the guide device 100 is known from the shape sensing data, and the length and orientation of the interventional instrument 150 is known or may be determined from the shape sensing data. The projected location will match the target location, or will be some determined distance and direction away from the target location. Accordingly, the processing unit 350 may control one of the first through seventh visual indicators 631-637 to illuminate, indicating direction in which the guide device 100 should be moved so that the interventional instrument 150, when advanced through the holder 120, will intersect the target. The user then manually repositions the guide device 100 as indicated by the illuminated visual indicator.

As mentioned above, other types of indicators may be incorporated to indicate a direction and amount of rotation and/or repositioning of the guide device 100, without departing from the scope of the present teachings. For example, the indicators may be audible indicators configured to emit sound to indicate the desired direction of rotation of the guide device 100 and/or a direction toward the desired position of the guide device 100. For example, different audible indicators may have different tone volumes and/or tone pitches to indicate a direction and/or amount of guide device 100 rotation or repositioning. Alternatively, the indicators may be haptic indicators configured to cause vibrations to indicate the desired direction of rotation of the guide device 100 and/or a direction toward the desired position of the guide device 100. For example, different haptic indicators may apply different vibration intensities to indicate a direction and/or amount of guide device 100 rotation or repositioning.

Another method to track the dynamic component of the interventional instrument 150 with the securable shape sensing device 140 is for the support structure 110 and the fastener 130 to be flexible, as mentioned above. The flexibility enables deformations in the support structure 110 and the shape sensing device 140 depending on either of the angular directions of the interventional instrument 150 when it is in the holder 120, adding degrees of freedom to the trajectory options provided by the holder 120. For example, when curvature of shape from the shape sensing data is used to locate the guide device 100, then the guide device 100 may be flexible, although a portion of it must maintain the shape template for identification. For example, referring to FIG. 6, as long as the guide device 100 is fairly rigid between the second visual indicator 632 and the fifth visual indicator 635, this sufficient to enable automatic location of the guide device 100 using the shape sensing data. The remainder of the guide device 100 may be more flexible, as long as the distances between the apex of the guide device 100 (e.g., at the first visual indicator 631) and the needle insertion point at the holder 120 are known. When axial strain or temperature changes are relied on to locate the guide device 100, then the guide device 100 may be more flexible throughout. However, the distance between a point in the guide device 100 where the shape sensing device 140 is located and the needle insertion point must still be known.

Figures 7A, 7B, 7C, 8A, 8B, 8C:
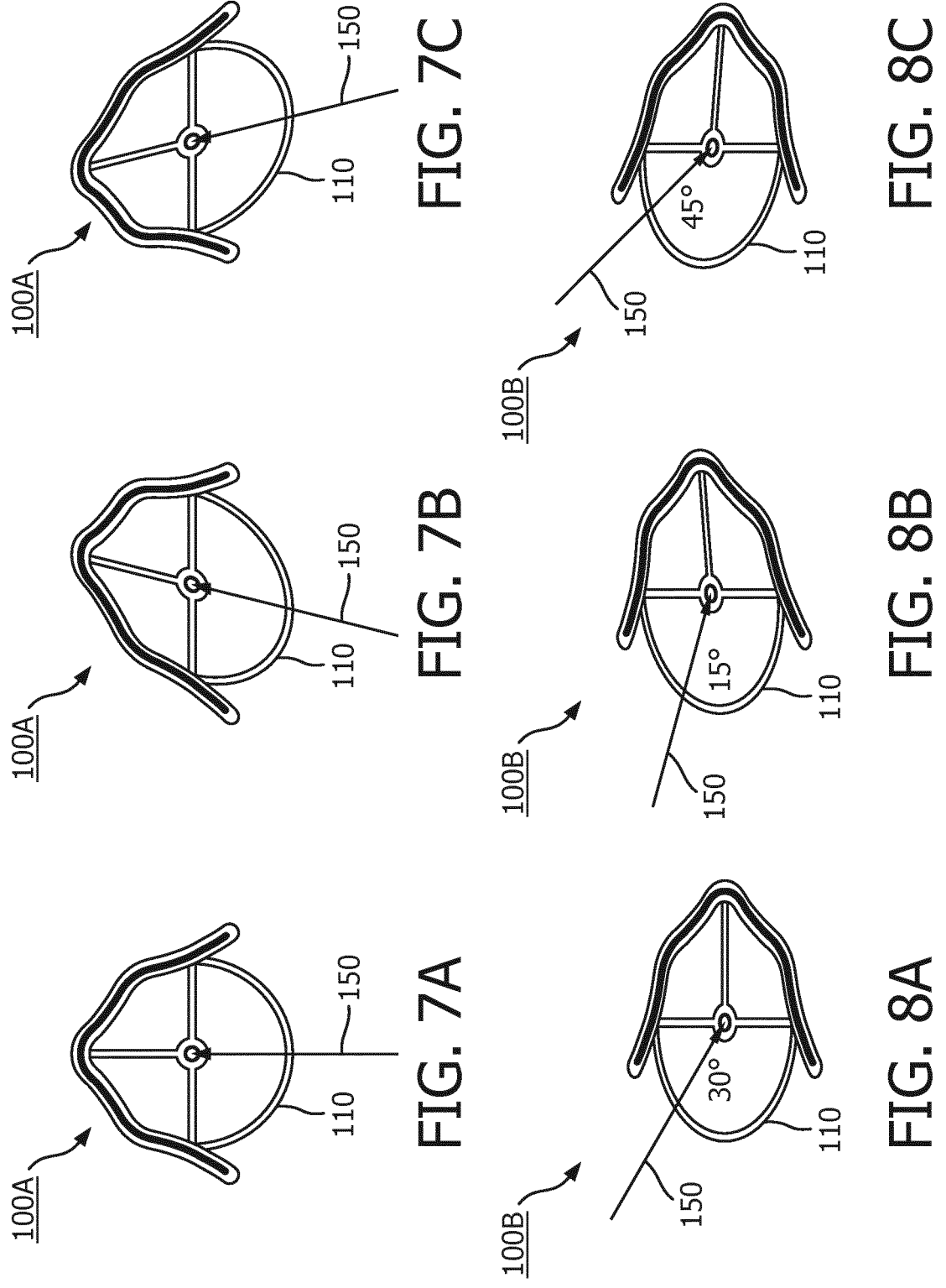
FIG. 7A is a plan view of a deformable guide device in a neutral orientation, according to a representative embodiment.
FIG. 7B is a plan view of a deformable guide device in a neutral orientation, according to a representative embodiment.
FIG. 7C is a plan view of a deformable guide device in a neutral orientation, according to a representative embodiment.
FIG. 8A is a plan view of a deformable guide device in a neutral orientation, according to a representative embodiment.
FIG. 8B is a plan view of a deformable guide device in a neutral orientation, according to a representative embodiment.
FIG. 8C is a plan view of a deformable guide device in a neutral orientation, according to a representative embodiment.

FIGS. 7A, 7B and 7C are plan views of a deformable guide device 100A that is deformable in a lateral (right and left) direction, according to a representative embodiment. All or part of the support structure 110 of the deformable guide device 100A is formed of a flexible material, such as silicone rubber, for example. The deformable guide device 100A is otherwise the same as the guide device 100, discussed above. Although not shown, it is understood that a shape sensing device 140, such as OSS device, would be secured to a portion of the support structure 110 of the deformable guide device 100A for providing shape sensing data.

FIG. 7A shows the deformable guide device 100A in a neutral orientation with the interventional instrument 150 at some selected entry trajectory. FIG. 7B shows the deformable guide device 100A skewed to the right, while the interventional instrument 150 remains at the selected entry trajectory, enabling the interventional instrument 150 to be adjusted to enter the subject at an angle to the right of a centerline of the deformable guide device 100A. Similarly, FIG. 7C shows the deformable guide device 100A skewed to the left, while the interventional instrument 150 remains at the selected entry trajectory, enabling the interventional instrument 150 to be adjusted to enter the subject at an angle to the left of the centerline.

FIGS. 8A, 8B and 8C are plan views of a deformable guide device 100B that is deformable in a longitudinal (up and down) direction, according to a representative embodiment. Again, all or part of the support structure 110 of the deformable guide device 100B is formed of a flexible material, such as silicone rubber, for example. The deformable guide device 100B is otherwise the same as the guide device 100, discussed above. Although not shown, it is understood that a shape sensing device 140, such as OSS device, would be secured to a portion of the support structure 110 of the deformable guide device 100B.

FIG. 8A shows the deformable guide device 100B in a neutral orientation with the interventional instrument 150 at a 30 degree entry trajectory. FIG. 8B shows the deformable guide device 100B skewed downwardly for a shallower insertion of the interventional instrument 150, enabling an entry trajectory of the interventional instrument 150 to be adjusted to 15 degrees. FIG. 8C shows the deformable guide device 100B skewed upwardly for a steeper insertion of the interventional instrument 150, enabling an entry trajectory of the interventional instrument 150 to be adjusted to 45 degrees. In the depicted example, the deformable guide device 100B remains neutral in the lateral direction, such that the interventional instrument 150 enters the subject along the centerline of the deformable guide device 100B. In an embodiment, a deformable guide device may be configured for both lateral and longitudinal deformation, combining the attributes of the deformable guide devices 100A and 100B.

An alternative form of visualization may be in the form of back-projection onto the subject's skin. In this case, the initial image data may also include an optical image data of the subject's skin, which is also registered to the shape sensing data and the image data from the imaging device 320. The target location may then be displayed on the subject's skin, along with an adjustment metric for the guide device 100.

Figure 9:
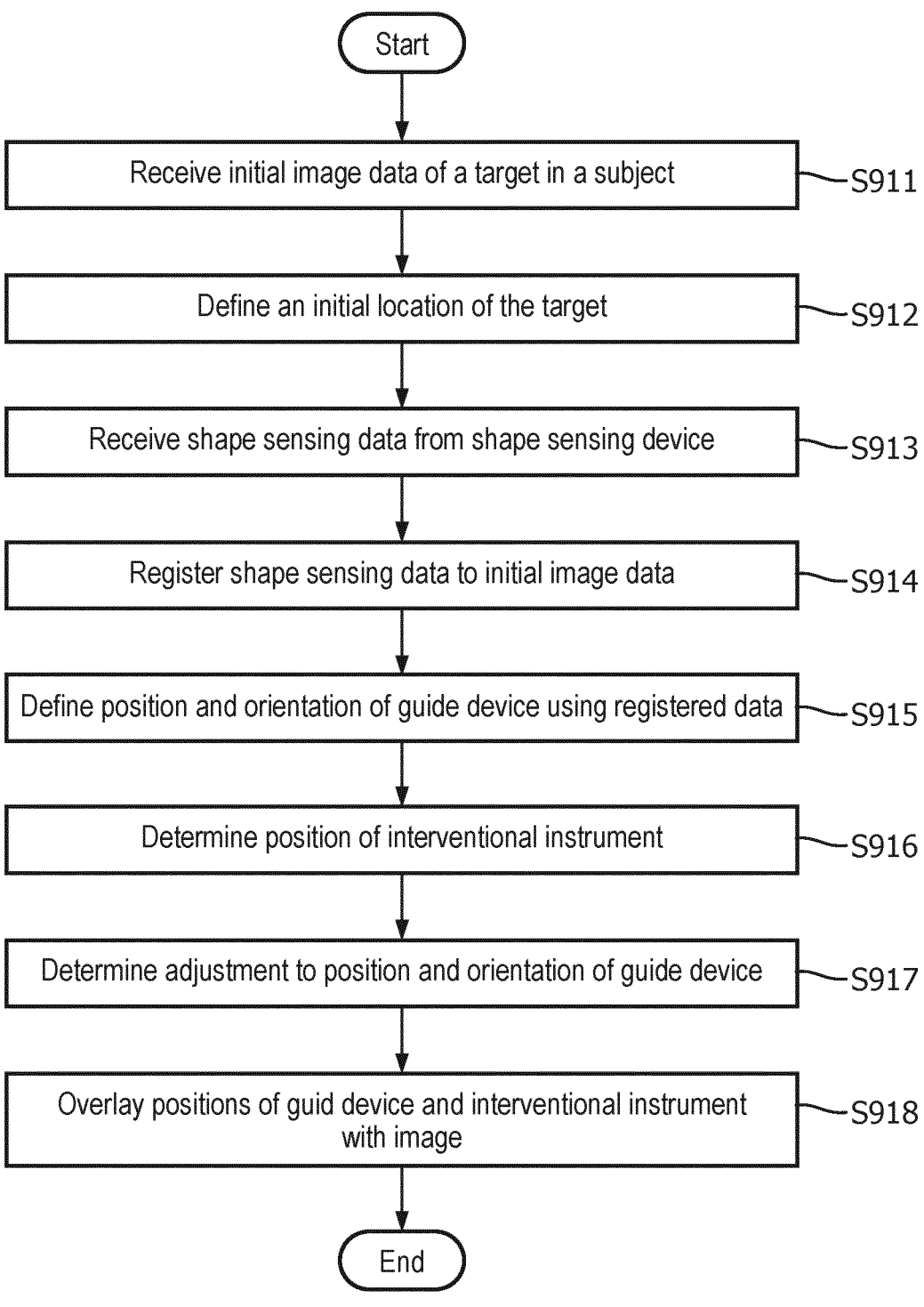
FIG. 9 is a flow diagram showing a method for guiding an interventional instrument to an internal target in a subject using a guide device and a shape sensing device, according to a representative embodiment.

FIG. 9 is a flow diagram showing a method for guiding an interventional instrument to an internal target in a subject using a guide device and a shape sensing device, according to a representative embodiment. The method may be implemented by computer readable instructions or computer code, e.g., stored the memory 352 and executable by the processing unit 350 of the processing unit 350, discussed above.

Referring to FIG. 9, image data of a target (t) in a subject (310) is received from an imaging device (320) in block S911, where the image data corresponds to an (initial) image of the subject taken by the imaging device. The image data may be x-ray, CT, fluoroscopy, ultrasound or MRI image data, for example, although other types of medical imaging capable of providing image data of an internal target may be incorporated. The image may also include an image of the guide device (100) on the subject. In block S912, a location of the target is defined in a 3D coordinate system using the image data, and stored in memory (352). Locating the target may be performed automatically by applying a shape recognition algorithm or automatic labeling of the anatomy to the image data, for example, or may be performed based on user input such as manually selecting a single point in the image to indicate the target site.

In block S913, shape sensing data is received from a shape sensing device (140), such as an OSS device, indicating a shape of a portion of the shape sensing device attached to or inserted through a fastener (130) of the guide device. The shape sensing data may be FORS data, for example. The shape sensing device, and hence the shape sensing data, are registered to the image data in block S914 so that the shape sensing device and images are within the same 3D coordinate system, as discussed above. Position and orientation of the guide device are defined with respect to the image data in block S915 using the registered shape sensing data. The position and orientation may be performed automatically using the shape sensing data from the shape sensing device, and stored in memory. Since the shape sensing device follows a known contour of the guide device (e.g., an upper portion of an outer frame of the guide device), specific characteristics of the guide device (e.g. curvature) can be identified as identifiable shape features using the shape sensing data. When the guide device is rigid or semi-rigid, the curvature profile of the guide device may be saved as a predefined template prior to the procedure. The received shape sensing data (S913) is processed and compared to the predefined template. A known matching algorithm (such as cross correlation, for example) is applied to identify the predefined template within the newly received shape sensing data. The position of the guide device is then determined to be the location along the shape sensing device where a match occurs, and the orientation of the guide device is then determined with respect to the position, e.g., based on the characteristics.

The unique shape characteristics of the outer frame of the guide device in the shape sensing data also assist in determining orientation. For example, when the guide device has a uniquely shaped protrusion (131) at an apex of the outer frame, the shape sensing data will capture the shape of the protrusion at a particular location, and the position and orientation of the guide device (having known dimensions) can be extrapolated from the protrusion location. To the extent the initial image data also shows the guide device, as mentioned above, a unique arrangement of cross-supports within the outer frame will visually indicate the orientation of the guide device. For example, a first cross-support (111) may connect a holder (channel guide) (120) with an apex of the outer frame, such that the first cross-support effectively points in the direction the interventional instrument will move as it is advanced through the holder. Alternatively, the positon and orientation of the guide device may be defined manually using a predefined template. Also, determining the position of the guide device may be done using the curvature/shape of the guide device and the shape sensing device attached to the guide device, or using axial strain/temperature. For example, a small heat sensor may be placed at one point along the guide device at which the shape sensing device comes in close proximity. Then, when there is a rise in axial strain due to an increase in temperature at that heat sensor location, the corresponding position of the guide device is known.

In block S916, a position of the interventional instrument is determined relative to the portion of the shape sensing device attached to or inserted through the fastener of the guide device using the shape sensing data and known dimensions of the guide device. Determining the position of the interventional instrument includes determining an entry point of a distal end of the interventional instrument at the holder and an entry trajectory of the interventional instrument, in the 3D coordinate system. The known dimensions may include, for example, the distance between the apex of the outer frame and the location of the holder, so that once the position of the apex is determined from the shape sensing data, the entry point may be extrapolated based on the distance to the holder. The entry trajectory may be determined based on a value of the entry trajectory selected and entered by the user. Alternatively, when the shape sensing device is connected to the proximal end of the interventional instrument, as shown in FIG. 1B, a length and entry trajectory of the interventional instrument may be calculated in real time using the shape sensing data without input by the user. Calculation of the entry trajectory is well known to one skilled in the art. For example, the distal end of the interventional instrument may be assumed to coincide with the position of the holder (entry point) in the 3D coordinate system as determined using the initial image data, and the proximal end of the interventional instrument may be determined using the shape sensing data in the same 3D coordinate system. The entry trajectory may then be determined using geometry to find the relationship between the distal and proximal ends of the interventional instrument. Alternatively, the user or a robot may define the entry trajectory based on the angles allowable by the holder.

In block S917, adjustments are optionally determined with regard to the position and orientation of the guide device and/or the trajectory angle of the interventional instrument, the calculation of which is also well known to one skilled in the art. For example, the initial location of the target is known from block S912, the initial position and orientation of the guide device are known from block S915, and the entry point and entry trajectory of the interventional instrument are known from block S916. Using the initial location of the target, the initial position and orientation of the guide device, and the entry point and entry trajectory of the interventional instrument, it can be geometrically determined whether the interventional instrument would intersect the target when advanced through the holder at the current entry trajectory. The calculated point at which the distal end of the interventional instrument would be positioned if advanced at the current entry trajectory from the guide device in the current position and orientation may be displayed on a display for the user to observe.

If it is determined that the distal end of the interventional instrument does not intersect the target location, a new position and/or orientation of the guide device are calculated in the 3D coordinate system from which the interventional instrument can be accurately advanced to the target at the known entry trajectory using geometric relationships between the known location of the target, the known entry trajectory, and alternative positions (movement of the guide device along the outer surface of the subject) and/or alternative orientations of the guide device (rotation of the guide device around the entry point). Alternatively, a new entry trajectory may be calculated in the 3D coordinate system at which the interventional instrument can be accurately advanced to the target at the existing position and orientation of the guide device, again using geometric relationships. Adjustments from the current positon and orientation to the new position and/or orientation, and/or adjustments to the entry trajectory, are then calculated based on offset(s) of current versus new positions, orientations and/or angles. The adjustments may be indicated to the user, e.g., by indicators and/or the display showing the direction and amount of rotation and/or movement of the guide device, and/or the amount of angular correction of the interventional instrument. The guide device may then be repositioned and/or reoriented, and/or the interventional instrument may be re-angled (e.g., by changing angle settings or by deformation of the guide device), following the calculated adjustments.

In block S918, indications of the determined positions of the guide device and the interventional instrument are overlaid with the initial image of the target on the display. Advancement of the interventional instrument is tracked using the shape sensing data, indications of which may also be displayed overlaid with the initial image. This enables a user or a robot to maneuver the interventional instrument to the target using the image data, that is, without requiring additional images by the imaging device.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Although developing adaptable predictive analytics has been described with reference to several exemplary embodiments, it is understood that the words that have been used are words of description and illustration, rather than words of limitation. Changes may be made within the purview of the appended claims, as presently stated and as amended, without departing from the scope and spirit of interventional procedure optimization in its aspects. Although developing adaptable predictive analytics has been described with reference to particular means, materials and embodiments, developing adaptable predictive analytics is not intended to be limited to the particulars disclosed; rather developing adaptable predictive analytics extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A system for guiding an interventional instrument to a target internal to a subject, the system comprising:
   a guide device configured to rest on an outer surface of the subject, the guide device comprising:
      at least one holder configured to receive the interventional instrument and to guide the interventional instrument to the target according to an entry trajectory;
      an outer frame forming an outer perimeter of the guide device, wherein the outer frame comprises at least one cross-support configured to attach the holder to the outer frame within the outer perimeter of the guide device; and
      a fastener attached to or attachable to a portion of the outer frame having a fixed shape with at least one identifiable shape feature; and
   a shape sensing device secured to the guide device by the fastener when the fastener is attached to the portion of the outer frame such that at least a portion of the shape sensing device secured to the guide device has the fixed shape with the at least one identifiable shape feature, the shape sensing device being arranged to provide shape sensing data relating to the fixed shape of the at least a portion of the shape sensing device secured to the guide device by the fastener, wherein a distal end of the shape sensing device is attached to the interventional instrument.

2. The system of claim 1, further comprising:
   a processing unit and memory for storing instructions that, when executed by the processing unit, cause the processing unit to:
   receive image data from an image including the target in the subject;
   define a location in a coordinate system of the target using the image data;
   receive the shape sensing data from the shape sensing device;
   determine a position and orientation of the guide device in the coordinate system using the shape sensing data;
   determine the position of the interventional instrument relative to the at least a portion of the shape sensing device secured to the guide device by the fastener, including an entry point and the entry trajectory of the interventional instrument, using the shape sensing data; and
   provide an indication of the determined position of the interventional instrument in the coordinate system, usable by a user interface to enable a user or a robot to maneuver the interventional instrument to the target.

3. The system of claim 2, wherein the guide device is connectable to an ultrasound probe configured to obtain ultrasound images of the interventional instrument in a region of interest and/or of the target, and
   wherein, when executed by the processing unit, the instructions further cause the processing unit to continuously update the location of the target and/or the entry trajectory using ultrasound image data from the ultrasound images.

4. The system of claim 2, wherein image data comprise:
   x-ray image data, CT image data, or fluoroscopy image data from an x-ray system, which is registered with the shape sensing device;
   ultrasound image data from an ultrasound system, which is registered with the shape sensing device; or comprise magnetic resonance imaging (MRI) image data from an MRI system, which is registered with the shape sensing device.

5. The system of claim 1, further comprising a processing unit and memory for storing instructions that, when executed by the processing unit, cause the processing unit to:

receive image data from an image including the target in the subject;

register the position and orientation of the guide device to the image data using the shape sensing data;

determine an adjustment of the guide device on the outer surface of the subject so that the entry trajectory of the interventional instrument will guide the interventional instrument to the target; and provide an adjustment parameter to enable implementation of the determined adjustment.

6. The system of claim 1, wherein the shape sensing device comprises an optical shape sensing device.

7. The system of claim 1, wherein the fastener comprises a sleeve, through which the shape sensing device is insertable, the sleeve being attached to or attachable to a portion of the outer frame defining at least one identifiable shape feature to enable detection of the guide device when the shape sensing device is inserted through the sleeve.

8. The system of claim 1, wherein the guide device is deformable in at least one of a lateral direction or a longitudinal direction, enabling adjusting of the interventional instrument.

9. The system of claim 1, wherein the at least one holder is arranged such that a plurality of discrete angular positions of the interventional instrument are selectable corresponding to a plurality of angles with respect to the outer surface of the subject.

10. The system of claim 1, wherein the at least one holder is arranged such that a plurality of discrete angular positions of the interventional instrument are selectable corresponding to a plurality of angles with respect to the outer surface of the subject.

11. The system of claim 1, wherein the at least one holder is arranged with a pivot joint movable through a continuous range of angles with respect to the outer surface of the subject.

12. The system of claim 1, wherein the at least one holder is arranged with a pivot joint movable through a continuous range of angles with respect to the outer surface of the subject.

13. The system of claim 1, further comprising:

a plurality of indicators on the guide device configured to indicate a desired direction of rotation and/or a desired position of the guide device on the outer surface of the subject.

14. The system of claim 13, wherein the plurality of indicators comprise:

a plurality of light emitting diodes (LEDs) configured to emit light to indicate the desired direction of rotation of the guide device and/or a direction of movement of the guide device toward the desired position;

a plurality of audible sensors configured to emit sound to indicate the desired direction of rotation of the guide device and/or a direction of movement of the guide device toward the desired position; or a plurality of haptic sensors configured to cause vibrations to indicate the desired direction of rotation of the guide device and/or a direction movement of the guide device toward the desired position.

15. The system of claim 13, further comprising a processing unit programed to enable determination of a position and orientation of the guide device on the outer surface of the subject based on the shape sensing data.

16. The system of claim 1, further comprising a processing unit programed to enable determination of a position and orientation of the guide device on the outer surface of the subject based on the shape sensing data.

17. The system of claim 16, further comprising:

a display interfacing with the processing unit for displaying a representation of the guide device overlaid with an image including the target in the subject.

18. The system of claim 1, further comprising a processing unit programmed to enable determination of a position of the interventional instrument relative to the at least a portion of the shape sensing device secured to the guide device, including an entry point and the entry trajectory of the interventional instrument.

19. The system of claim 18, further comprising:

a display interfacing with the processing unit for displaying a representation of the interventional instrument overlaid with an image including the target in the subject.

20. A system for guiding an interventional instrument to a target internal to a subject, the system comprising:

a guide device configured to rest on an outer surface of the subject, the guide device comprising:

at least one holder configured to receive the interventional instrument and to guide the interventional instrument to the target according to an entry trajectory; and an outer frame forming an outer perimeter of the guide device, wherein the outer frame comprises at least one cross-support configured to attach the holder to the outer frame within the outer perimeter of the guide device;

a fastener attached or attachable to a portion of the outer frame having a fixed shape with at least one identifiable shape feature;

an optical shape sensing (OSS) device secured to the guide device by the fastener when the fastener is attached to the portion of the outer frame such that at least a portion of the OSS device secured to the guide device has the fixed shape with the at least one identifiable shape feature, wherein a distal end of the OSS device is attached to the interventional instrument; and a processing unit and memory for storing instructions that, when executed by the processing unit, cause the processing unit to:

receive image data from an image of the target in the subject;

define a location of the target using the image data;

receive shape sensing data from the OSS device indicating a shape of the at least a portion of the OSS device secured to the guide device;

determine a position and orientation of the guide device using the shape sensing data; and cause an indication of a position of the interventional instrument overlaid with the image of the target to be displayed on a display, enabling maneuvering of the interventional instrument to the target using the image data.

21. The system of claim 20, wherein, when executed by the processing unit, the instructions further cause the processing unit to:

determine a position of the interventional instrument relative to the at least a portion of the OSS device secured to the guide device, including an entry point and the entry trajectory of the interventional instrument, using the shape sensing data.

22. The system of claim 20, wherein the guide device is deformable in at least one of a lateral and a longitudinal direction, enabling adjusting of the interventional instrument.

23. The system of claim 20, wherein the instructions further cause the processing unit to:

register the position and orientation of the guide device to the image data using the shape sensing data;

determine an adjustment of the guide device on the outer surface of the subject so that the entry trajectory of the interventional instrument will guide the interventional instrument to the target; and provide an adjustment parameter for maneuvering the interventional instrument to the target.

24. A system for guiding an interventional instrument to a target internal to a subject, the system comprising:

a guide device configured to rest on an outer surface of the subject, the guide device comprising:

at least one holder configured to receive the interventional instrument and to guide the interventional instrument to the target according to an entry trajectory; and an outer frame forming an outer perimeter of the guide device, wherein the outer frame comprises at least one cross-support configured to attach the holder to the outer frame within the outer perimeter of the guide device, and wherein a portion of the outer frame has a predetermined shape with at least one identifiable shape feature;

a fastener attached to the portion of the outer frame having the predetermined shape, wherein the fastener adopts the predetermined shape of the portion of the outer frame with the at least one identifiable shape feature; and a shape sensing device secured to the guide device by the fastener when the fastener is attached to the portion of the outer frame such that at least a portion of the shape sensing device secured to the guide device has the fixed shape with the at least one identifiable shape feature, the shape sensing device being arranged to provide shape sensing data relating to the fixed shape of the at least a portion of the shape sensing device secured to the guide device by the fastener.

* * * * *